(12) United States Patent
Prema Mohanasundaram et al.

(10) Patent No.: US 12,161,309 B2
(45) Date of Patent: Dec. 10, 2024

(54) ARTICULATING MECHANISM FOR THE LAPAROSCOPIC ABLATION DEVICE FOR BLUNT DISSECTION

(71) Applicant: Covidien LP, Mansfield, MA (US)

(72) Inventors: Suresh Kumar Prema Mohanasundaram, Chennai (IN); Sunny Kumar, Hyderabad (IN)

(73) Assignee: Covidien LP, Mansfield, MA (US)

( * ) Notice: Subject to any disclaimer, the term of this patent is extended or adjusted under 35 U.S.C. 154(b) by 1071 days.

(21) Appl. No.: 17/031,127

(22) Filed: Sep. 24, 2020

(65) Prior Publication Data

US 2022/0087665 A1    Mar. 24, 2022

(51) Int. Cl.
*A61B 17/00* (2006.01)

(52) U.S. Cl.
CPC ............... *A61B 17/00234* (2013.01); *A61B 2017/00296* (2013.01); *A61B 2017/00539* (2013.01); *A61B 2017/00544* (2013.01)

(58) Field of Classification Search
CPC ............... A61B 17/00234; A61B 2017/00296
USPC .......................................................... 606/1
See application file for complete search history.

(56) References Cited

U.S. PATENT DOCUMENTS

| | | | |
|---|---|---|---|
| 4,202,352 A | 5/1980 | Osborn | |
| 5,057,494 A | 10/1991 | Sheffield | |
| 5,321,113 A | 6/1994 | Cooper et al. | |
| 5,330,502 A | 7/1994 | Hassler et al. | |
| 5,358,496 A | 10/1994 | Ortiz et al. | |
| 5,431,323 A | 7/1995 | Smith et al. | |
| 5,575,799 A * | 11/1996 | Bolanos | A61B 17/0684 606/208 |
| 5,725,536 A | 3/1998 | Oberlin et al. | |
| 6,003,517 A * | 12/1999 | Sheffield | A61B 18/1447 606/41 |
| 6,007,550 A | 12/1999 | Wang et al. | |
| 6,086,586 A | 7/2000 | Hooven | |
| 6,436,107 B1 | 8/2002 | Wang et al. | |
| 6,533,784 B2 | 3/2003 | Truckai et al. | |
| 6,656,177 B2 | 12/2003 | Truckai et al. | |
| 6,786,382 B1 | 9/2004 | Hoffman | |
| 6,802,843 B2 | 10/2004 | Truckai et al. | |
| 6,835,336 B2 | 12/2004 | Watt | |
| 6,913,579 B2 | 7/2005 | Truckai et al. | |
| 7,111,769 B2 | 9/2006 | Wales et al. | |
| 7,398,707 B2 | 7/2008 | Morley et al. | |
| 7,721,934 B2 | 5/2010 | Shelton, IV et al. | |
| 7,726,537 B2 | 6/2010 | Olson et al. | |
| 7,780,054 B2 | 8/2010 | Wales | |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

PCT Search Report and Written Opinion issued in PCT/US2021/052080 dated Dec. 22, 2021, 12 pages.

*Primary Examiner* — Nadia A Mahmood
(74) *Attorney, Agent, or Firm* — Weber Rosselli & Cannon LLP

(57) ABSTRACT

A surgical apparatus is described herein including an articulating segmented endoscopic portion including at least two segments connected by an angled rotary interface.

20 Claims, 10 Drawing Sheets

(56) References Cited

U.S. PATENT DOCUMENTS

| | | |
|---|---|---|
| 7,947,000 B2 | 5/2011 | Vargas et al. |
| 7,955,315 B2 | 6/2011 | Feinberg et al. |
| 8,335,359 B2 | 12/2012 | Fidrich et al. |
| 8,337,515 B2 | 12/2012 | Viola et al. |
| 8,397,971 B2 | 3/2013 | Yates et al. |
| 8,579,176 B2 | 11/2013 | Smith et al. |
| 8,706,184 B2 | 4/2014 | Mohr et al. |
| 8,827,934 B2 | 9/2014 | Chopra et al. |
| 8,915,940 B2 | 12/2014 | Steege et al. |
| 8,961,499 B2 | 2/2015 | Paik et al. |
| 8,968,187 B2 | 3/2015 | Kleyman et al. |
| 9,289,225 B2 | 3/2016 | Shelton, IV et al. |
| 9,375,268 B2 | 6/2016 | Long |
| 9,470,297 B2 | 10/2016 | Aranyi et al. |
| 9,480,492 B2 | 11/2016 | Aranyi et al. |
| 9,801,630 B2 | 10/2017 | Harris et al. |
| 9,918,659 B2 | 3/2018 | Chopra et al. |
| 10,004,498 B2 | 6/2018 | Morgan et al. |
| 10,004,558 B2 | 6/2018 | Long et al. |
| 10,085,746 B2 | 10/2018 | Fischvogt |
| 10,172,973 B2 | 1/2019 | Vendely et al. |
| 10,194,897 B2 | 2/2019 | Cedro et al. |
| 10,206,686 B2 | 2/2019 | Swayze et al. |
| 10,292,758 B2 | 5/2019 | Boudreaux et al. |
| 10,349,938 B2 | 7/2019 | Widenhouse et al. |
| 10,373,719 B2 | 8/2019 | Soper et al. |
| 10,376,178 B2 | 8/2019 | Chopra |
| 10,390,899 B2 | 8/2019 | Malkowski et al. |
| 10,405,753 B2 | 9/2019 | Sorger |
| 10,478,162 B2 | 11/2019 | Barbagli et al. |
| 10,480,926 B2 | 11/2019 | Froggatt et al. |
| 10,524,866 B2 | 1/2020 | Srinivasan et al. |
| 10,555,788 B2 | 2/2020 | Panescu et al. |
| 10,569,071 B2 | 2/2020 | Harris et al. |
| 10,603,106 B2 | 3/2020 | Weide et al. |
| 10,610,306 B2 | 4/2020 | Chopra |
| 10,638,953 B2 | 5/2020 | Duindam et al. |
| 10,639,114 B2 | 5/2020 | Schuh et al. |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,716,637 B2 | 7/2020 | Kowshik et al. |
| 10,729,886 B2 | 8/2020 | Fenech et al. |
| 10,743,751 B2 | 8/2020 | Landey et al. |
| 10,772,485 B2 | 9/2020 | Schlesinger et al. |
| 10,779,803 B2 | 9/2020 | Prisco et al. |
| 10,792,022 B2 | 10/2020 | Keast et al. |
| 10,792,464 B2 | 10/2020 | Romo et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,856,855 B2 | 12/2020 | Gordon |
| 10,881,385 B2 | 1/2021 | Fenech |
| 10,885,630 B2 | 1/2021 | Li et al. |
| 2002/0147462 A1 | 10/2002 | Mair et al. |
| 2003/0013972 A1 | 1/2003 | Makin |
| 2003/0032948 A1 | 2/2003 | Dubrowskij |
| 2004/0120981 A1 | 6/2004 | Nathan |
| 2004/0260334 A1 | 12/2004 | Braun |
| 2005/0165276 A1 | 7/2005 | Belson et al. |
| 2006/0235457 A1 | 10/2006 | Belson |
| 2007/0135803 A1 | 6/2007 | Belson |
| 2008/0045938 A1 | 2/2008 | Weide et al. |
| 2013/0096385 A1 | 4/2013 | Fenech et al. |
| 2013/0303945 A1 | 11/2013 | Blumenkranz et al. |
| 2014/0035798 A1 | 2/2014 | Kawada et al. |
| 2014/0052018 A1 | 2/2014 | Hawkins |
| 2014/0235943 A1 | 8/2014 | Paris et al. |
| 2015/0148690 A1 | 5/2015 | Chopra et al. |
| 2015/0265368 A1 | 9/2015 | Chopra et al. |
| 2016/0001038 A1 | 1/2016 | Romo et al. |
| 2016/0067450 A1 | 3/2016 | Kowshik |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2016/0331358 A1 | 11/2016 | Gordon |
| 2016/0374676 A1 | 12/2016 | Flanagan et al. |
| 2017/0020628 A1 | 1/2017 | Averbuch |
| 2017/0112571 A1 | 4/2017 | Thiel et al. |
| 2017/0112576 A1 | 4/2017 | Coste-Maniere et al. |
| 2017/0112588 A1 | 4/2017 | Bissing et al. |
| 2017/0209071 A1 | 7/2017 | Zhao et al. |
| 2017/0224338 A1 | 8/2017 | Sung |
| 2017/0238795 A1 | 8/2017 | Blumenkranz et al. |
| 2017/0258309 A1 | 9/2017 | Deyanov |
| 2017/0265952 A1 | 9/2017 | Donhowe et al. |
| 2017/0274189 A1 | 9/2017 | Smith et al. |
| 2017/0311844 A1 | 11/2017 | Zhao et al. |
| 2017/0319165 A1 | 11/2017 | Averbuch |
| 2018/0001058 A1 | 1/2018 | Schlesinger |
| 2018/0064904 A1 | 3/2018 | Vargas et al. |
| 2018/0078318 A1 | 3/2018 | Barbagli et al. |
| 2018/0144092 A1 | 5/2018 | Flitsch et al. |
| 2018/0153621 A1 | 6/2018 | Duindam et al. |
| 2018/0214138 A9 | 8/2018 | Prisco et al. |
| 2018/0221039 A1 | 8/2018 | Shah |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0076143 A1 | 3/2019 | Smith |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192143 A1 | 6/2019 | Shelton, IV et al. |
| 2019/0192234 A1 | 6/2019 | Gadda et al. |
| 2019/0200984 A1 | 7/2019 | Shelton, IV et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0223693 A1 | 7/2019 | Vargas |
| 2019/0231449 A1 | 8/2019 | Diolaiti et al. |
| 2019/0239723 A1 | 8/2019 | Duindam et al. |
| 2019/0239724 A1 | 8/2019 | Averbuch et al. |
| 2019/0239831 A1 | 8/2019 | Chopra |
| 2019/0246876 A1 | 8/2019 | Schaning |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0269885 A1 | 9/2019 | Bailey et al. |
| 2019/0272634 A1 | 9/2019 | Li et al. |
| 2019/0290375 A1 | 9/2019 | Dearden et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0328213 A1 | 10/2019 | Landey et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0008827 A1 | 1/2020 | Dearden et al. |

(56) References Cited

U.S. PATENT DOCUMENTS

| | | |
|---|---|---|
| 2020/0022767 A1 | 1/2020 | Hill et al. |
| 2020/0029948 A1 | 1/2020 | Wong et al. |
| 2020/0030044 A1 | 1/2020 | Wang et al. |
| 2020/0030461 A1 | 1/2020 | Sorger |
| 2020/0030575 A1 | 1/2020 | Bogusky et al. |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0069384 A1 | 3/2020 | Fenech et al. |
| 2020/0077870 A1 | 3/2020 | Dicarlo et al. |
| 2020/0077991 A1 | 3/2020 | Gordon et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0100776 A1 | 4/2020 | Blumenkranz et al. |
| 2020/0107894 A1 | 4/2020 | Wallace et al. |
| 2020/0109124 A1 | 4/2020 | Pomper et al. |
| 2020/0121170 A1 | 4/2020 | Gordon et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0146757 A1 | 5/2020 | Fenech et al. |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0222666 A1 | 7/2020 | Chan et al. |
| 2020/0229679 A1 | 7/2020 | Zhao et al. |
| 2020/0242767 A1 | 7/2020 | Zhao et al. |
| 2020/0261175 A1 | 8/2020 | Fenech |
| 2020/0268240 A1 | 8/2020 | Blumenkranz et al. |
| 2020/0275860 A1 | 9/2020 | Duindam |
| 2020/0289023 A1 | 9/2020 | Duindam et al. |
| 2020/0297442 A1 | 9/2020 | Adebar et al. |
| 2020/0305983 A1 | 10/2020 | Yampolsky et al. |
| 2020/0315554 A1 | 10/2020 | Averbuch et al. |
| 2020/0330795 A1 | 10/2020 | Sawant et al. |
| 2020/0345436 A1 | 11/2020 | Kowshik et al. |
| 2020/0352427 A1 | 11/2020 | Deyanov |
| 2020/0352675 A1 | 11/2020 | Averbuch |
| 2020/0364865 A1 | 11/2020 | Donhowe et al. |
| 2020/0367726 A1 | 11/2020 | Landey et al. |
| 2020/0383750 A1 | 12/2020 | Kemp et al. |
| 2020/0391010 A1 | 12/2020 | Fenech et al. |
| 2020/0406002 A1 | 12/2020 | Romo et al. |
| 2021/0000524 A1 | 1/2021 | Barry et al. |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 | 12/2008 |
| CZ | 486540 | 9/2016 |
| CZ | 2709512 | 8/2017 |
| CZ | 2884879 | 1/2020 |
| EP | 1644519 B1 | 12/2008 |
| EP | 2141497 A1 | 1/2010 |
| EP | 3326551 A1 | 5/2018 |
| EP | 3367915 A4 | 7/2019 |
| EP | 3413830 A4 | 9/2019 |
| EP | 3576598 A1 | 12/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | 03005028 A | 1/2004 |
| MX | 03000137 A | 9/2004 |
| MX | 03006874 A | 9/2004 |
| MX | 225663 B | 1/2005 |
| MX | 226292 | 2/2005 |
| MX | 03010507 A | 7/2005 |
| MX | 05011725 A | 5/2006 |
| MX | 06011286 | 3/2007 |
| MX | 246862 B | 6/2007 |
| MX | 2007006441 A | 8/2007 |
| MX | 265247 | 3/2009 |
| MX | 284569 B | 3/2011 |

\* cited by examiner

ARTICULATING MECHANISM FOR THE LAPAROSCOPIC ABLATION DEVICE FOR BLUNT DISSECTION

FIELD

The present technology is generally related to a surgical apparatus for minimally invasive surgical procedures including articulating features.

BACKGROUND

Minimally invasive surgical procedures involve the deployment of instrumentation through small openings in a wall of body tissue. This type of surgery is highly advantageous because trauma to the patient is substantially reduced, which also reduces recovery time, costs, and the risk of post-operative complications. For convenience, as hereinafter used the term "endoscopic" shall refer generally to all types of minimally invasive surgical procedures, including laparoscopic procedures.

Endoscopic instruments can include articulation capabilities; however, it can be difficult to effectively operate and/or control the articulating portion of the instrument during the surgical procedure from outside the body. For example, providing and/or maintaining an adequate amount of force in or around the area of articulation can be difficult, e.g., because the tissue can provide resistance against the articulation which in some instances can limit the range of articulation, cause the articulating means to fail or slip during articulation, and/or cause at least partial reversal of the articulation over time, specifically after a surgeon's hand is removed from the instrument.

There remains a need for methods and devices which allow minimally invasive surgical procedures to be performed with enhanced stability of an articulated configuration of the surgical instrument thereby maximizing the range of articulation, reducing or preventing failure or slipping of the articulating means, and/or limiting the range of reversal of the articulation. Efficiency of the surgical procedure can also be improved by freeing the surgeon's hands for other surgical related activities.

SUMMARY

The present disclosure describes a surgical apparatus for use in minimally invasive surgical procedures including at least one articulating feature. The surgical apparatus includes a non-endoscopic portion and an endoscopic portion. The endoscopic portion includes at least first and second segments connected by at least one angled rotary interface joint. The first segment includes a first proximal end portion operatively connected to the non-endoscopic portion and a first distal end portion having a first beveled gear and a second beveled gear positioned therein. The second beveled gear is positioned between the first beveled gear and an angled gear affixed on a second proximal end portion of the second segment.

In some embodiments, the first beveled gear includes a first set of alternating teeth and slots configured to mechanically interact with a second set of alternating teeth and slots of the second beveled gear, and the second set of alternating teeth and slots are also configured to mechanically interact with a third set of alternating teeth and slots of the angled gear. The angled gear is a non-beveled gear. In some embodiments, the angled gear is an angled spur gear.

In some embodiments, the first segment includes a first outer wall defining a first lumen along a first longitudinal axis defined between the first proximal end portion and the first distal end portion of the first segment. The first and second beveled gears are maintained within the first lumen.

In some embodiments, the first beveled gear faces distally along the first longitudinal axis and includes a rotary driver extending proximally therefrom along the first longitudinal axis to the non-endoscopic portion. In some embodiments, the second beveled gear is positioned on a post positioned distal to the first beveled gear, the post extending generally perpendicular to the first longitudinal axis and affixed on an inner surface of the first outer wall.

The first segment and/or the outer wall of the first segment can further include an angled circumferential channel defined therethrough. The channel is configured to receive at least a portion of the angled gear.

In some embodiments, the angled gear includes a set of alternating teeth and slots extending radially outward from a side of the angled gear. In some embodiments, the set of alternating teeth and slots extending radially outward from a side of the angled gear are received within the angled circumferential channel.

In some embodiments, the first distal end portion of the first segment further includes a first angled edge spaced distally from the angled circumferential channel. The first angled edge configured to form a first half of an angled interface.

In some embodiments, the second segment includes a second outer wall defining a second lumen along a second longitudinal axis defined between the second proximal end portion and a second distal end portion. The second segment is configured to rotate about the angled rotary interface joint relative to the first segment. In some embodiments, the second longitudinal axis and the first longitudinal axis are collinear when the endoscopic portion is straight. In some embodiments, the second longitudinal axis of the second segment is about 90° relative to the first longitudinal axis of the first segment.

In some embodiments, the second proximal end portion of the second segment further includes a second angled edge. The second angled edge being spaced distally from the angled gear by a gap defined by a sidewall having a second length. The second angled edge configured to form a second half of an angled interface. The first and second angled edges in combination forming an angled interface.

In addition to the first and second segments, the endoscopic portion of the surgical apparatus also includes a distal operating portion operatively coupled to a second distal end portion of the second segment. The distal operating portion can include a surgical unit selected from the group consisting of a surgical stapler unit, surgical retractor unit, surgical sealer unit, surgical ablation unit, or clip applier unit.

In some embodiments, the surgical apparatus described herein includes a non-endoscopic portion and an endoscopic portion having at least first and second segments connected by at least one angled rotary interface joint including a first beveled gear, a second beveled gear, and an angled non-beveled gear, wherein the first beveled gear drives the angled non-beveled gear via the second beveled gear.

Methods of using the surgical apparatus described herein in minimally invasive surgical procedures are also provided.

BRIEF DESCRIPTION OF THE DRAWINGS

Various embodiments are described herein by way of example in conjunction with the following figures.

DETAILED DESCRIPTION

The surgical apparatus described herein includes features to provide for rotary articulation of a distal endoscopic portion thereof. The articulation features may be employed on a variety of endoscopic instruments such as clip appliers, staplers, graspers, tissue retractors, tissue sealers, shears, dissectors, manipulators, pushers, and the like.

Figure 1A:
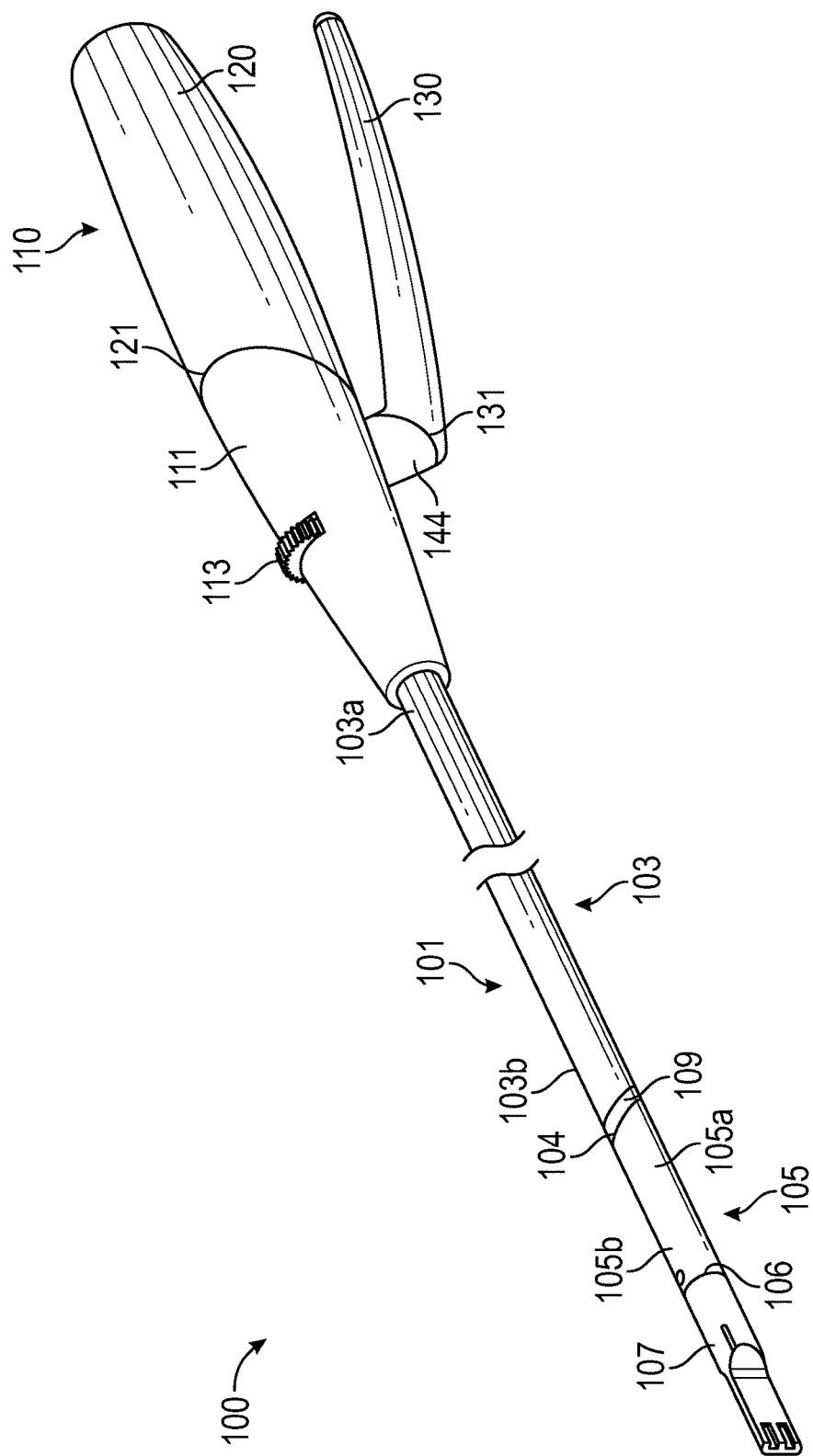
FIG. 1A is a perspective view of an endoscopic portion of a surgical apparatus as described in at least one embodiment herein.

Referring to FIG. 1A, surgical apparatus 100 includes an endoscopic portion 101 and a non-endoscopic handle portion 110. The endoscopic portion 101 is an elongated tubular member including at least a first segment 103, a second segment 105, and a distal operating portion 107. The first segment 103 includes a first proximal end portion 103a operatively connected to the non-endoscopic handle portion 110 and a first distal end portion 103b connected to a second proximal end portion 105a of the second segment 105 by a rotatable angled interface, joint 104, which is configured as shown in more detail in FIGS. 2A-3E. The first distal end portion 103b also includes an angled circumferential channel 109 defined therethrough, the channel 109 being located proximal to the angled interface or joint 104. A second distal end portion 105b of the second segment 105 terminates in the distal operating portion 107, which may optionally separately articulate at second joint 106. The surgical apparatus 100 and/or the distal operating portion 107 as shown in FIG. 1A is a surgical stapler and/or includes a stapling unit, respectively.

Figure 1B:
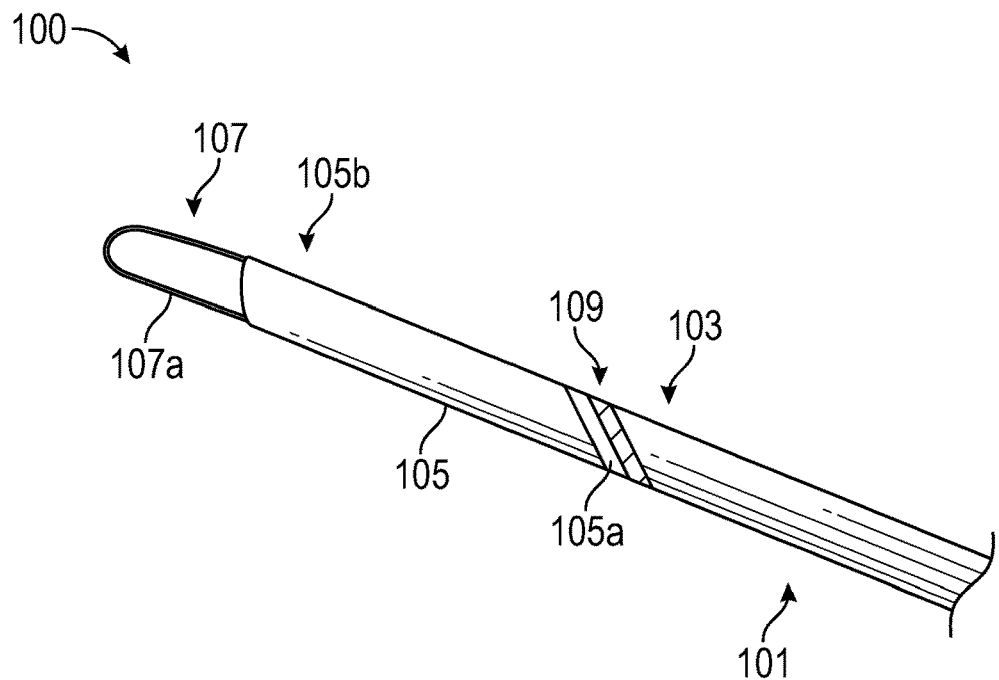
FIG. 1B is a partial perspective view of a distal end of an endoscopic portion of a surgical apparatus as described in at least one embodiment herein.

In some embodiments, as shown in FIG. 1B, the surgical apparatus 100 is a surgical retractor (such as the Endo Peanut® manufactured by Medtronic) wherein the distal operating portion 107 is a surgical retractor unit including a disposable piece of sterile material or "peanut" 107a, such as rolled mesh gauze or a cotton swab, fixed in place over the second distal end portion 105b of the second segment 105. The piece of material can be designed for a variety of uses including, but not limited to, swabbing fluids, controlling bleeding, blunt dissection of soft tissue for separating tissue layers, or retracting tissue.

Figure 2A:
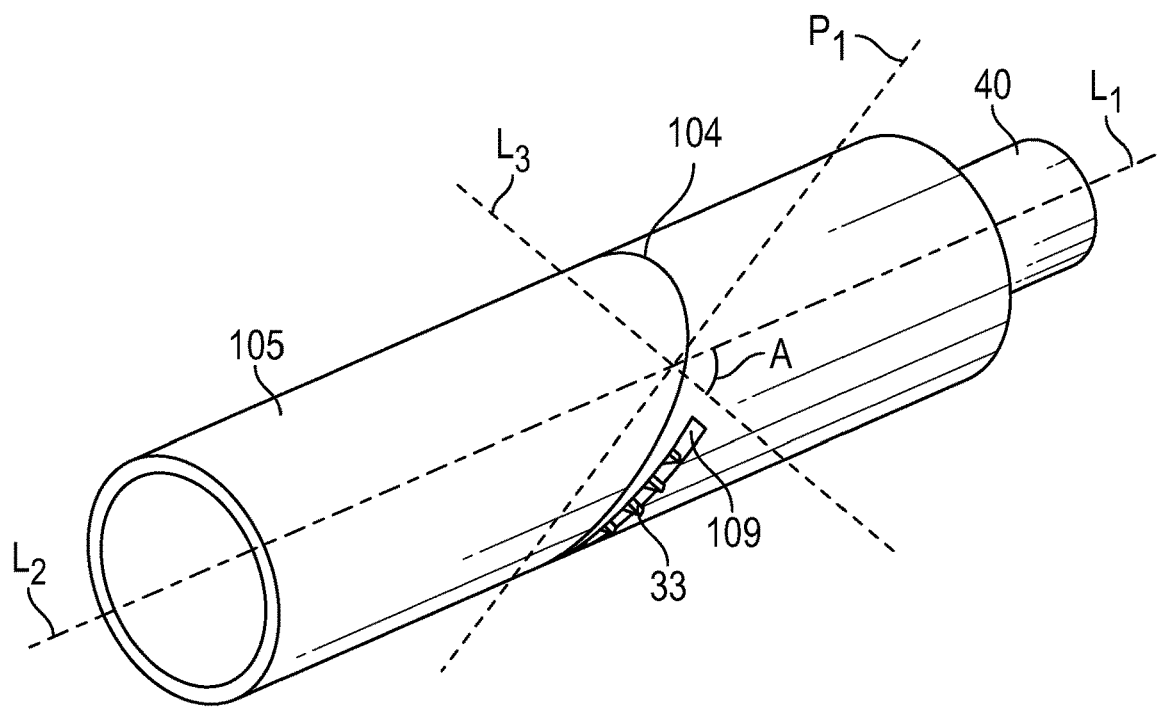
FIGS. 2A-2C are perspective views of an articulating endoscopic portion of a surgical apparatus showing an angled rotary interface as described in at least one embodiment herein.

Referring to FIG. 2A, the angled rotary interface joint 104 joining the first and second segments 103 and 105 is shown. The first segment 103 defines a first longitudinal axis $L_1$. The second segment 105 defines a second longitudinal axis $L_2$. The rotary interface 104 defines a geometric plane $P_1$ which is angled with respect to the first longitudinal axis $L_1$. An axis of rotation $L_3$ extends perpendicularly from plane $P_1$ and is angled from first axis $L_1$ at an angle A, wherein A can be from about 1° to about 60°, in some embodiments from about 25° to about 55°, in some other embodiments from about 30° to about 50°, and in still some other embodiments about 45°.

Figure 2B:
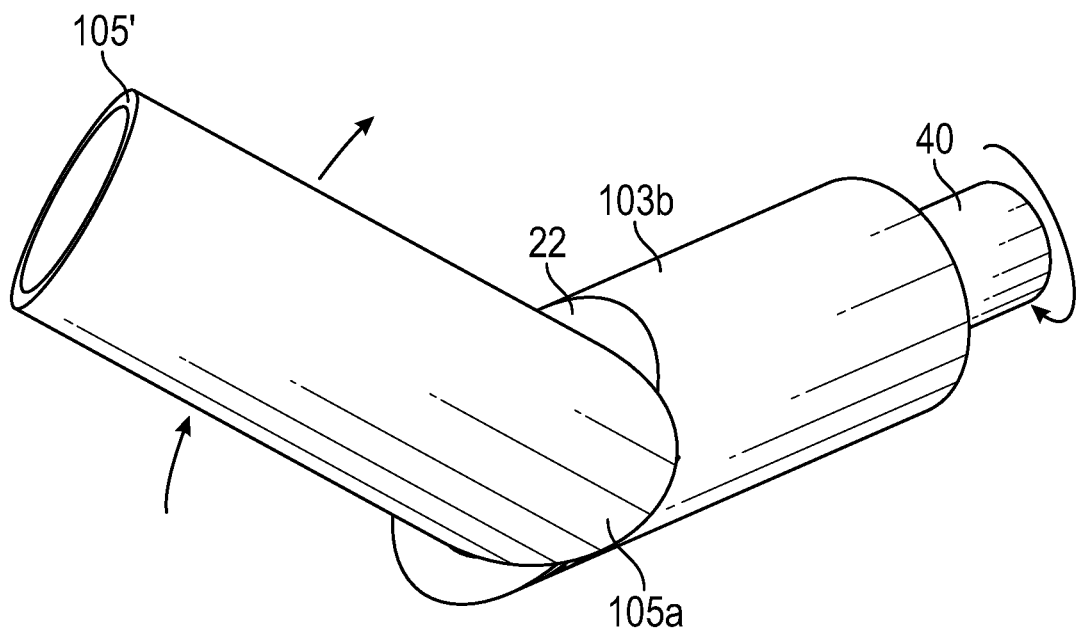

As can be seen from FIG. 2B, the second segment 105 is rotatable around axis $L_3$ such that the path traced by axis $L_2$ defines a substantially conical geometric surface. At least at one position, the second axis $L_2$ is collinear with axis $L_1$ so that the endoscopic portion 101 is configured as a long, straight tube which can be disposed through a trocar cannula (See FIGS. 2A and 8). Once the endoscopic portion 101 has been positioned in a cannula such that the second segment 105 is beyond the distal end of the cannula and located entirely within the body cavity, the second segment 105 may be rotated or articulated relative to the first segment 103 in order to configure the second segment 105 at an angle from the first segment 103. For example, referring to FIGS. 2A-2C, upon rotation of the rotary driver 40 (as indicated by the arrows) the second segment 105 may be moved from its initial collinear position to a position designated as 105' wherein it is angled from the first segment 103. The maximum angle between the position at 105' and the initial collinear position is achieved by 180° rotation of the second segment 105 and is equal to twice the angle A of axis $L_3$. Thus, if axis $L_3$ is angled at 45° from $L_1$, the second segment 105 may be moved to a 90° angle from its original position, as shown specifically in FIG. 2C.

This articulation of the second segment 105 with the distal operating portion presents many advantages. For example, it allows the endoscopic portion 101 to be inserted through a cannula, yet also permits the instrument, after insertion, to be configured to angled shapes. This permits the surgeon to gain access to body tissue which is otherwise difficult to reach.

FIGS. 3A-3F illustrate a joint configuration to permit such angled rotation of an endoscopic portion as described above. The first segment 103 includes a first outer wall 20 defining a first lumen 21 extending along the first longitudinal axis $L_1$. As depicted, in some embodiments, the first segment 103 or first outer wall 20 is generally circular in cross. However, it is envisioned that the first segment or first outer wall may define any polygonal cross-section, including, but not intended to be limited to, elliptical, pentagonal, hexagonal, octagonal, etc. A distal most end of the distal end portion 103b of the first segment 103 includes a first angled edge 22 defining the first plane $P_1$ creating a first outer angle $oa_1$ between the first plane $P_1$ and the first longitudinal axis $L_1$. The first angled edge 22 defines an edge opening 25. The edge opening 25 designed to accommodate the initial passage of the angled gear 33 into the first segment 103 and the channel 109 while maintaining the ability to prevent removal of the angled gear 33 from the first segment 103 and channel 109 thereafter. In some embodiments, the edge opening 25 defines a narrower opening in cross-section (or diameter) than the first lumen 21. In some embodiments, the edge opening 25 is generally the same size as the gear lumen 37 or the inner perimeter of the gap sidewall 35 to ensure a snug or firm coupling therebetween while maintaining the ability to rotate or articulate.

The first distal end portion 103b of the first segment 103 also includes an angled circumferential channel 109 defined completely through the first outer wall 20. The angled circumferential channel 109 defines a second geometric plane $P_2$ creating a first inner angle $ia_1$ relative to the first longitudinal axis $L_1$. In some embodiments, the first and second planes $P_1$, $P_2$ are parallel to each other. In some embodiments, the first inner and outer angles $ia_1$, $oa_1$ are supplementary angles.

As depicted, the angled circumferential channel 109 extends around a majority, i.e., greater than about 50% of the outer perimeter of the first segment 103 along the second plane $P_2$. In some embodiments, the angled circumferential channel 109 extends between about 55% to about 95% of the outer perimeter of the first segment 103 along the second plane $P_2$. In some embodiments, the angled circumferential channel 109 extends between about 60% to about 80% of the outer perimeter of the first segment 103 along the second plane $P_2$.

Figure 3A:
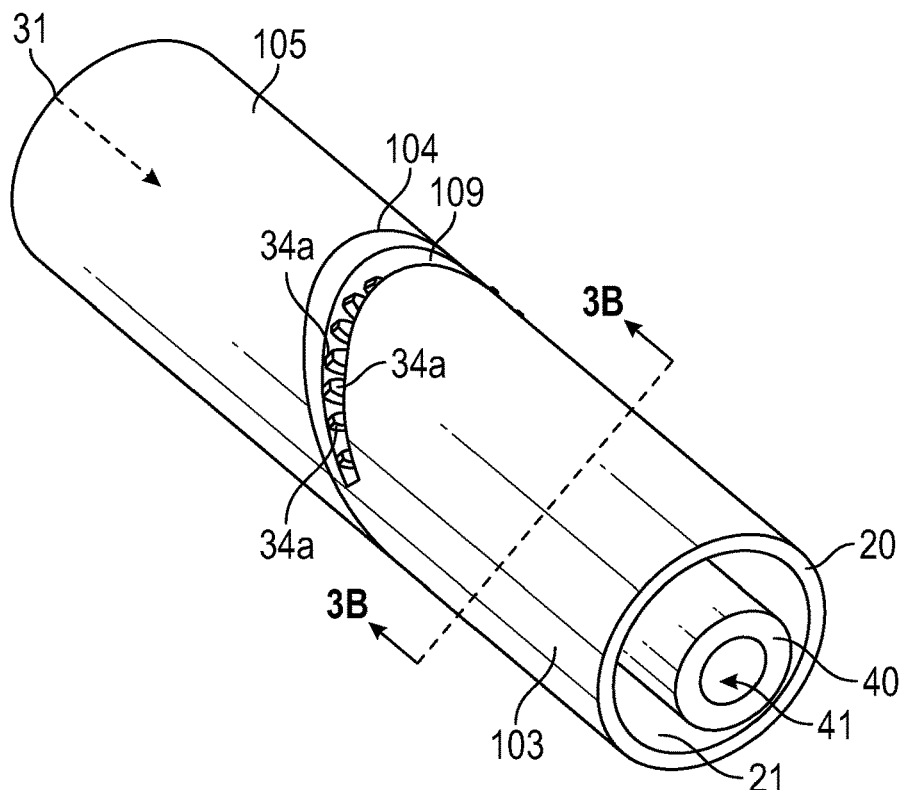
FIGS. 3A and 3C-3E are perspective views of endoscopic portions, collectively or separately, of a surgical apparatus as described in at least one embodiment herein.
Figure 3B:
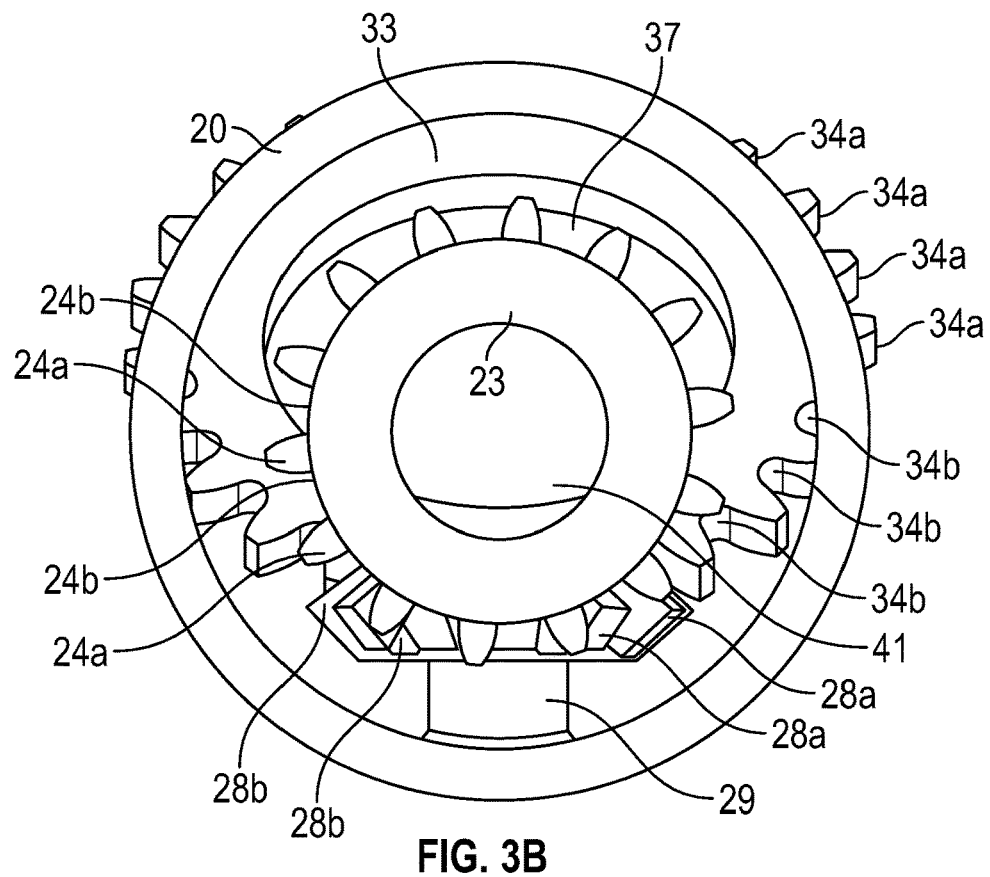
FIG. 3B is cross-sectional end view of the surgical apparatus of FIG. 3A and showing an angled rotary interface joint including a first beveled gear, a second beveled gear, and an angled gear as described in at least one embodiment herein.
Figure 3C:
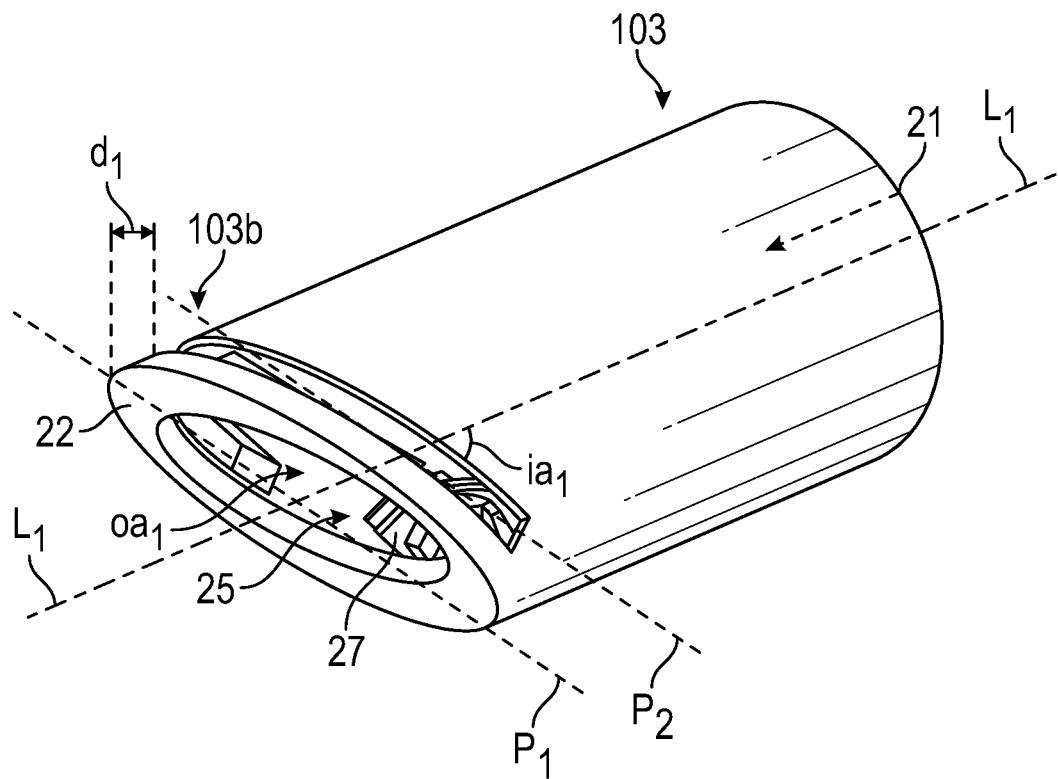
Figure 3D:
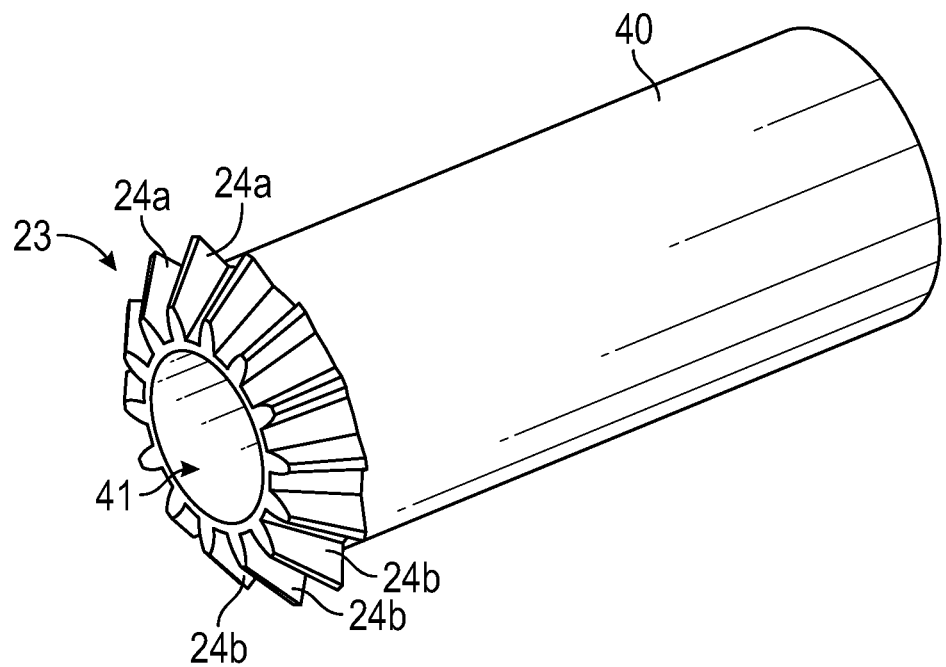

As further depicted specifically in FIGS. 3B and 3C, both the first beveled gear 23 and the second beveled gear 27 are positioned and/or maintained within the first lumen 21 of the first segment 103, and particularly in the first distal end portion 103b of the first segment 103 immediately prior to the first angled edge 22. The first beveled gear 23 includes a first set of alternating teeth 24a and slots 24b configured to mechanically interact with a complimentary second set of alternating teeth 28a and slots 28b of the second beveled gear 27. The first beveled gear 23 is positioned to face distally inside the lumen and includes a hollow tubular rotary driver 40 extending proximally along the first longitudinal axis $L_1$ and operatively connected to the non-endoscopic handle portion 110. The rotary driver 40 includes a driver lumen 41 extending through the first beveled gear 23. The rotary driver 40 being configured to rotate the first beveled gear 23. For example, as described in more detail hereinbelow, in some embodiments, rotary driver 40 may be manually rotated by the user or surgeon by means of an actuator ring 113 rotatably mounted to the non-endoscopic portion 110 and having an exterior surface for user actuation. Alternatively, in some embodiments, the rotary driver 40 may be auto-driven wherein the rotary driver is connected to an automated electrical system and power source, as known in the art, via the non-endoscopic portion.

The second beveled gear 27 includes a second set of alternating teeth 28a and slots 28b configured to mechanically interact with both the first set of alternating teeth 24a and slots 24b of the first beveled gear 23 and a third set of alternating teeth 31a and slots 31b of the angled gear 30. The second beveled gear 27 is maintained on a post 29 fixed to an inner surface of the first outer wall 20 and extending therefrom in a direction generally perpendicular to the first longitudinal axis $L_1$. In some embodiments, the first and second beveled gears generally face each other perpendicularly.

Figure 3E:
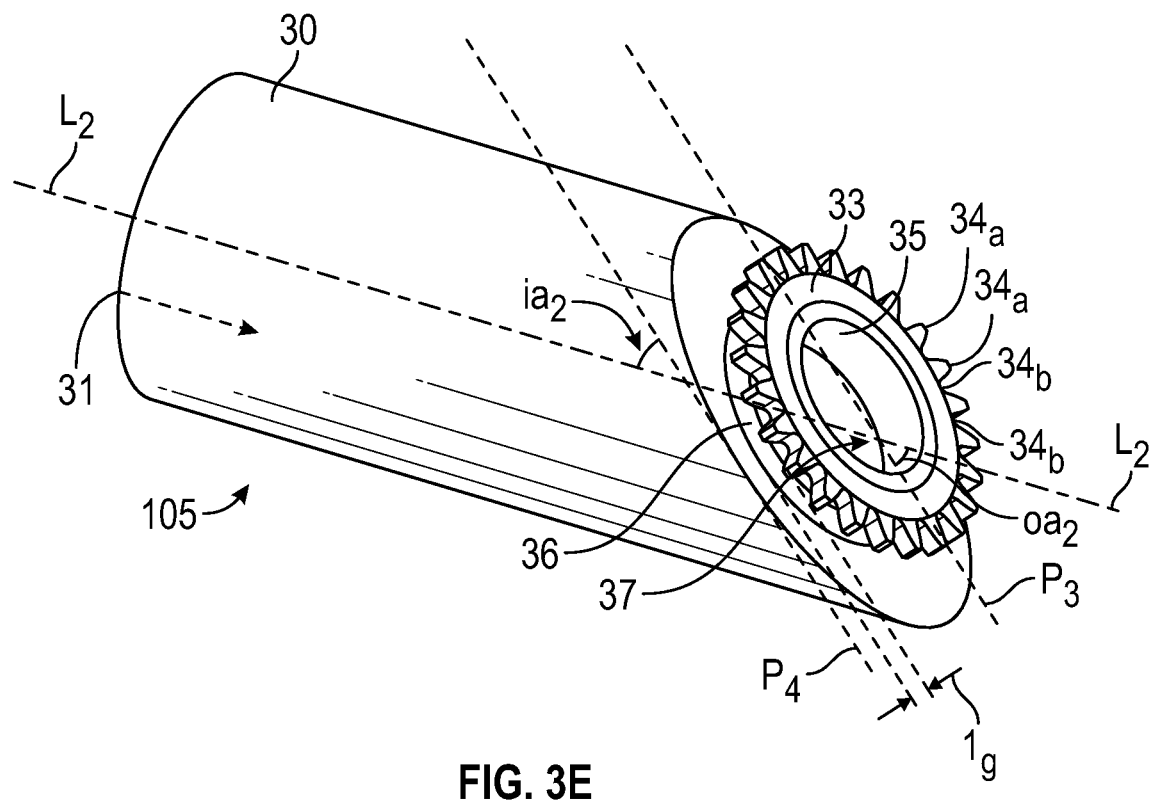

As further shown in FIG. 3E, the second segment 105 includes a second outer wall 30 defining a second lumen 31 extending along the second longitudinal axis $L_2$. As depicted, in some embodiments, the second segment 105 or second outer wall 30 is generally circular in cross-section. However, it is envisioned that the second segment or second outer wall may define any polygonal cross-section, including but not limited to, elliptical, pentagonal, hexagonal, octagonal, etc. A proximal most end of the second proximal end portion 105a of the second segment 105 includes the angled gear 33 including the third set of alternating teeth 34a and slots 34b configured to mechanically interact with the second set of alternating teeth 28a and slots 28b of the second beveled gear 27. In some embodiments, the angled gear 33 is a spur gear. The angled gear 33 defines a third geometric plane $P_3$ forming a second outer angle $oa_2$ between the third plane $P_3$ and the second longitudinal axis $L_2$.

In some embodiments, the third geometric plane $P_3$ defined by the angled gear 33 is parallel to or aligned with the second geometric plane $P_2$ of the channel 109. In some embodiments, the third geometric plane $P_3$ defined by the angled gear 33 is not parallel or not aligned perfectly the second geometric plane $P_2$ of the channel 109.

The angled gear 33 is spaced from a second angled edge 32 by a spacer wall 35 defining a gap 36 therebetween. The length $l_g$ of the gap 36 between the second angled edge 32 and the backside of the angled gear 33 being generally equal a thickness of first angled edge 22 and/or the distance di between the first angled edge 22 and the angled circumferential channel 109 of the first segment 103, such that the first and second segments 103, 105 remain tightly coupled to each other when the angled gear 33 is located, at least partially if not predominantly, within the angled circumferential channel 109.

The second angled edge 32 defines a fourth geometric plane $P_4$ creating a second inner angle $ia_2$ relative to the second longitudinal axis $L_2$. In some embodiments, the third and fourth planes $P_3$, $P_4$ are parallel to each other. In some embodiments, the second inner and outer angles $ia_2$, $oa_2$ are supplementary angles. In some embodiments, the first and fourth planes $P_1$, $P_4$ are parallel to or aligned with each other and the second and third planes $P_2$, $P_3$ are parallel to or aligned with each other.

As further depicted in FIG. 3E, in some embodiments, the angled gear 33 includes a gear lumen 37 extending through at least the thickness of the angled gear 33 and the length $l_g$ of the gap 36. In some embodiments, the gear lumen 37 defines a narrower opening in cross-section (or diameter) than the second lumen 31.

As further depicted in FIG. 3B, in some embodiments, at least a portion, if not predominantly or entirely, of the driver lumen 41 and the gear lumen 37 share a common longitudinal axis and/or are collinear. It is envisioned that in such embodiments, additional electrical and/or mechanical parts (not shown), such as a push rod or electrical cable, can be passed therethrough operatively connecting the non-endoscopic handle portion 110 and the distal operating portion 107 therebetween.

In some embodiments, a pushrod 50 extends longitudinally through the joint 104 and connects an actuator 113 in the handle portion 110 with the distal operating portion 107. The pushrod 50 can operate by reciprocating motion or by rotation. The pushrod can be super elastic in order to permit flexing at the joint while providing for actuation of the distal operating portion. Various types of metal alloys are known in the art, for example shape memory alloys, may be used to fabricate the push rod.

In some embodiments, the angled gear 33 is centered on the second proximal end portion 105a of the second segment 105. In some embodiments, the angled gear 33 is offset from a center of the second proximal end portion 105a of the second segment 105.

When the first and second segments 103, 105 are coupled as depicted in FIG. 3A, a portion of the third set of alternating teeth 34a and slots 34b may extend within the angled circumferential channel 109 and may further extend beyond the channel 109 and beyond an outer surface of the first outer wall 20. In the embodiments wherein the angled circumferential channel 109 is completely open, at least a portion of the angled gear 33 and the third set of alternating teeth 34a and slots 34b can be potentially exposed to and/or clogged by surrounding bodily fluids and/or tissue when inside the body.

Figure 4:
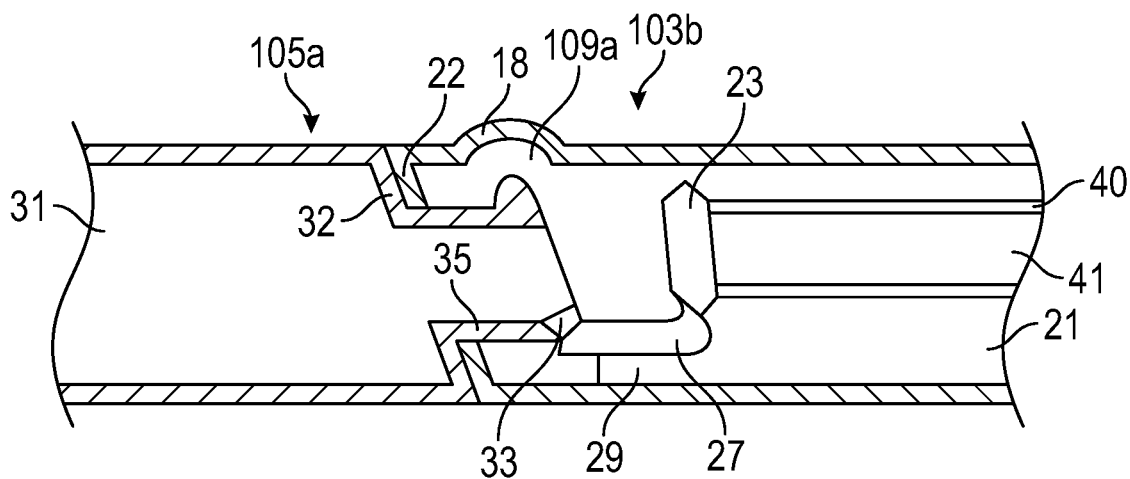
FIG. 4 is a cross-sectional side view of a closed articulating endoscopic portion of a surgical apparatus as described in at least one embodiment herein.

In some embodiments, as shown in FIG. 4, the angled circumferential channel 109a is closed and covered by a bridge wall 18 which spans the channel 109a and creates a bump out to the outer surface of the first outer wall 20. The bridge wall 18 is configured to prevent access of tissue or bodily fluids into the channel 109a without interfering with the rotation of the angled gear 33 and third set of alternating teeth 34a and slots 34b inside the first segment 103. Although not depicted, in an alternative embodiment, the open angled circumferential channel (see FIGS. 2A-3C) can be covered with an outer flexible sheath which can be secured to or simply slid over at least a portion of the outer surface of the first segment to cover the channel. The flexible sheath can be made of any suitable sterilizable material and can include but not be limited to polyethylene, nylon, fluorinated ethylene propylene (FEP), TEFLON, polyethylene terephthalate (PET), or polycarbonate.

The combination and/or configuration of the three gears as described herein provides a more stable and efficient articulating joint configured to withstand a greater amount of resistance inside the body. For example, by fixing the non-beveled gear (e.g., a spur gear) at an angle, and particularly and obtuse angle, relative to the second beveled gear (as opposed to perpendicular to a gear), the second and third different sets of alternating teeth and slots can interact more efficiently thereby reducing skipping or failure of the joint during articulation. In another example, by spacing the first beveled gear (e.g., the drive gear) from the angled gear via the second beveled gear, any resistance is spread over the entirety of the gear configuration (as opposed to a single location) thereby reducing localized strain and again reducing skipping or failure of the joint during articulation. Also, by the first segment includes a channel and the angled gear including radially outward extending teeth and grooves configured to be received within the channel, the overall size of the angled gear can be maximized while remaining positioned within the first lumen of the first segment thereby enhancing the overall strength of the articulating joint, the joint is less likely to get jammed or slip gears, as compared to joints wherein only two angled gears directly interact with each other, and more particularly wherein a beveled gear interacts directly with a crown gear. The enhanced stability can increase efficiency of the surgical apparatus and can also decrease the likelihood of reversal of the articulation upon removal of the surgeon's hand from the apparatus, especially as compared to articulating joints wherein only two angled gears directly interact with each other, and more particularly wherein a beveled gear interacts directly with an angled crown gear.

Figure 2C:
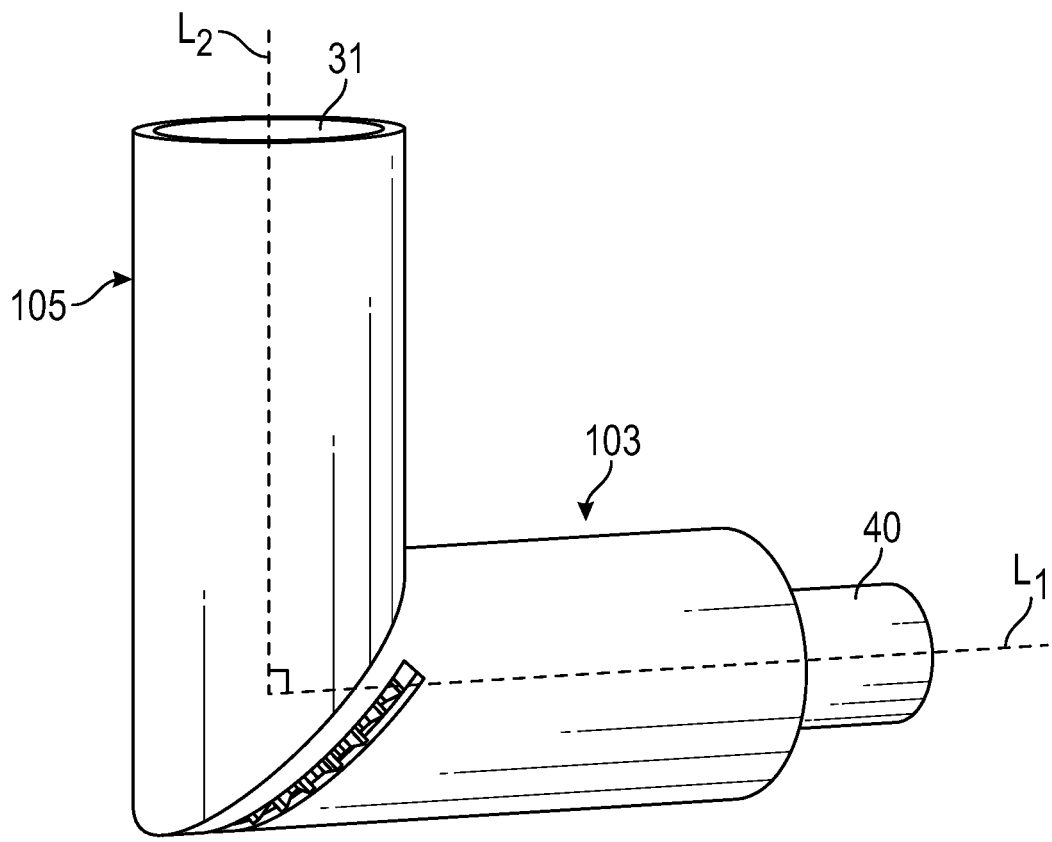
Figure 5:
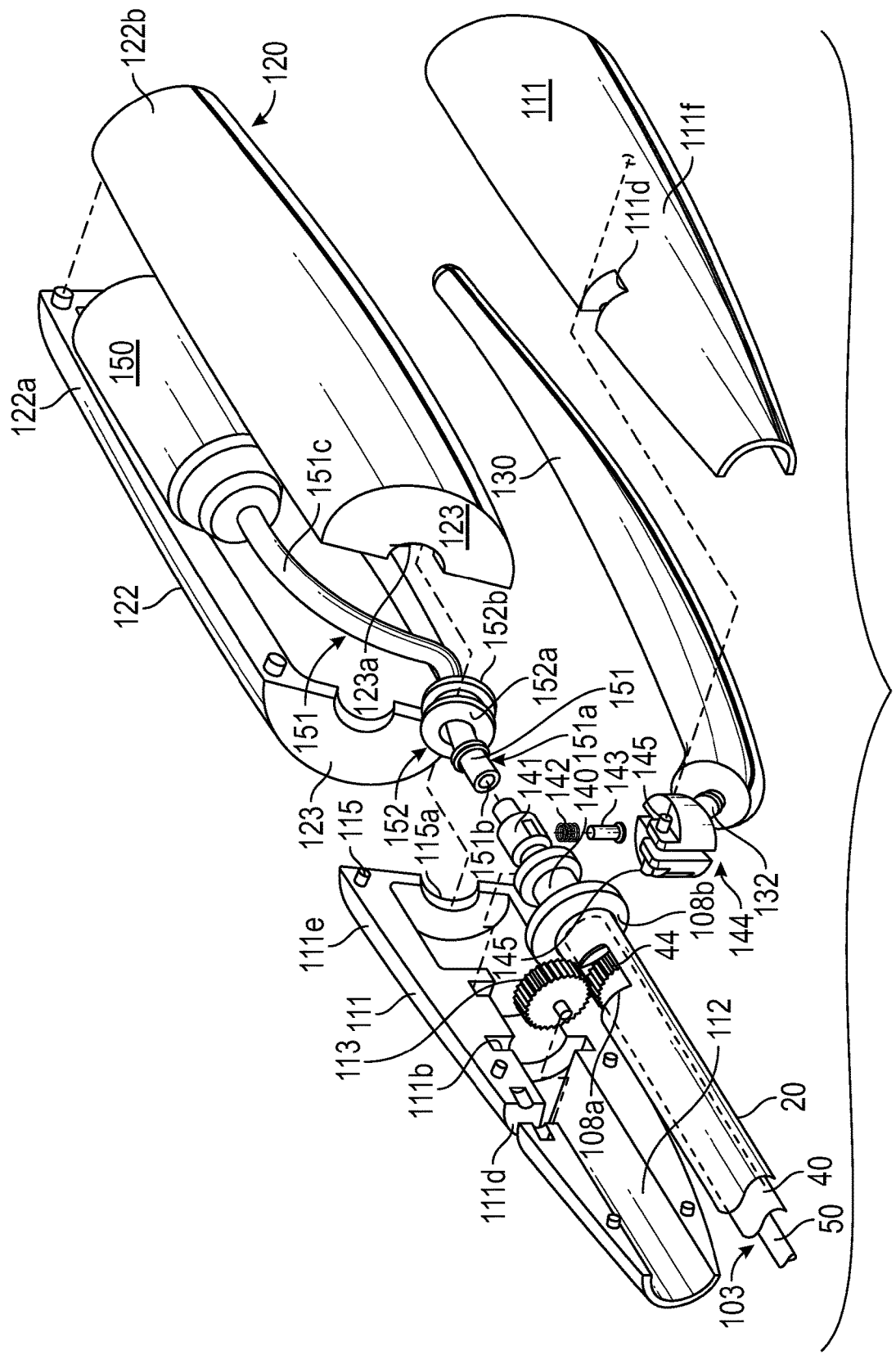
FIG. 5 is an exploded perspective view of a non-endoscopic portion of the surgical apparatus of FIG. 1A.

Referring now to FIGS. 1, 4, and 5, in some embodiments, the non-endoscopic handle portion 110 can include at least a body portion 111, a handle grip 120, and trigger 130. The body portion 111 may be fabricated as two halves 111e and 111f which may be assembled to form body portion 111 and includes an axial bore 112 in which the first proximal end portion of the first segment 103 is disposed. First segment 103 includes the first outer wall 20, and the rotary drive tube 40. As mentioned above, the rotary drive tube 40 is a cylindrical member having the first set of teeth 24a on the first beveled gear 23 at the distal end thereof for engaging corresponding set of slots 28b of the second beveled gear 27. The second beveled gear 27 further includes a second set of teeth 28a for engaging corresponding slots 34b on the angled gear 33 causing the second segment 105 to achieve articulation and/or rotation of the second segment 105, as shown in FIGS. 2A-2C. The proximal end portion of the rotary drive tube 40 possesses a circumferential array of longitudinally oriented notches 44 which function as a spur gear. A slot 108a is provided in the proximal end portion of the first outer wall 20 to allow access to the gear 44, with which it is aligned vertically.

Annular seals 52a and 52b prevent the passage of gas or other fluids through the apparatus. Seals 52a and 52b are preferably fabricated from a synthetic polymeric material and may be lubricated with a biocompatible lubricant grease, such as a silicone or a solid lubricant, or they may be self-lubricating by having a low coefficient of friction or by containing a lubricant within the structure of the seal material.

Rotary actuator 113 includes a disk-shaped member mounted in slot 111d in the body portion and having axles 113a rotatably mounted within slots 111a in the body portion and aligned in parallel with the axis of the instrument. The upper portion of the disk-shaped member of the rotary actuator 113 extends beyond the surface of the body portion 111 to allow actuation by a user's finger. The lower portion of the disk-shaped member extends through slot 108a to contact the rotary driver 40. The periphery of the disk portion includes gear teeth 113b which engage the corresponding notches 44 of the rotary driver. Thus, mechanical rotation of rotary actuator 113 by the surgeon causes rotation of the rotary drive tube 140, which, in turn, causes rotating articulation of the second segment 105 around angled joint 104.

Optionally, a click-stop feature 160 may be included which comprises a plunger 161 slidably disposed within slot 163 and resiliently biased by spring 162 into engagement with corresponding slits (not shown) arrayed on the proximal surface of disk-shaped rotary actuator 113. The distal tip of plunger 161 is rounded to permit disengagement when a sufficient turning force has been applied to rotary actuator 113. The biasing force of the spring 162 is adapted for releasable engagement of the click-stop mechanism 160 by selecting a suitable spring 162 such that the position of the rotary actuator 113 (and second segment 105) is stabilized against free spinning and unintended movement of the actuator 113. Movement is easily accomplished when the surgeon actuates the rotary actuator 113, and the click-stop feature 160 provides audible as well as tactile indication when a certain position has been reached.

The proximal end of outer tube 108 includes a flange 108b which is fixedly mounted to a slot 111b in the body portion.

Push rod 50 is operatively connected to drive cylinder 140, which is disposed within bore 112 of the body portions. In some embodiments, the drive cylinder 140 is pneumatically powered and has an internal movable piston (not shown) which drives the push rod 50 with a reciprocating motion for actuating the distal operating portion 107. Optionally, a rotary motion can be employed, in conjunction with a linear cam or barrel cam. Suitable pneumatic drive cylinder devices are known to those with skill in the art and are commercially available.

The pneumatic drive cylinder 140 is controlled by switching unit 141 which includes a valve mechanism. Plunger 143 is mounted to the switching unit 141 and operates a valve for controlling the flow of compressed gas to drive pneumatic cylinder 140. Plunger 143 is resiliently biased by spring 142 to a closed-valve position. Trigger mount 144 is pivotally mounted to body portion 111 by means of pivot pins 145.

Trigger 130 is an elongated member having a projection 132 adapted for rotatable engagement with a corresponding slot in trigger mount 144 such that trigger 130 may be pivoted with respect to trigger mount 144.

The cam member 144 includes a bottom surface 146 which is angled with respect to the longitudinal axis of the body portion 111. Likewise, the trigger 130 includes a surface 132 angled with respect to the lengthwise extension of the trigger 130. Surfaces 132 and 146 are in slidable contact to form angled rotary interface 131. Pivoting trigger 130 around an axis of rotation defined by projection 132 will move trigger between differently angled positions with respect to body portion 111.

Pressing of the trigger 130 causes trigger mount 144 to pivot around pins 145 and contact the plunger 143. Further pressing of the trigger moves the plunger 143 against the biasing force of spring 142 to open the valve in drive switching unit 141. This permits the flow of compressed gas to drive the pneumatic drive cylinder 140.

The compressed gas may be provided by a compressed gas storage bottle 150 mounted in the interior of handle grip 120. The handle grip 120 is an elongated generally cylindrical member 122 which may be fabricated as two mating halves 122a and 122b which join to form an enclosure for mounting the gas bottle 150. A flexible tube 151 extends from the gas bottle 150 through axial bore in the rotatable coupling 152 to switching unit 141 and carries compressed gas thereto. Tube 151 possesses a rotating seal 151a which permits tube portions 151b and 151c to rotate relative to each other without the tube 151 pinching closed.

Body portion 111 possesses a proximal wall 115 oriented at an angle with respect to the longitudinal axis of the body portion. Handle grip 120 possesses a distal wall 123 which is oriented at an angle with respect to the longitudinal axis of the handle grip. Walls 115 and 123 face each other in sliding contact to form an angled rotary interface 121 similar in operational features to rotary interface 104. That is, handle grip 120 may be rotated relative to body portion 111 to move from a position in linear alignment with the body portion 111, as shown in FIG. 4, to a position in which it is angled from the body portion, as shown in FIGS. 6 and 7.

To permit rotation around rotary interface 121 a rotatable coupling 152 is provided. Coupling 152 is disposed through centrally located apertures 123a and 115a in the distal and proximal walls 123 and 115, respectively, and possesses circumferential flanges 152a and 152b which abut the inner surfaces of the facing walls 115 and 123 in the vicinity of apertures 115a and 123a. Thus, wall 123 of the handle grip 100 and wall 115 of the body portion are held in slidable contact and are rotatable with respect to each other around an axis defined by the rotatable coupling 152. Rotatable coupling 152 also possess a central bore for passage of tube 151 therethrough.

Figure 6:
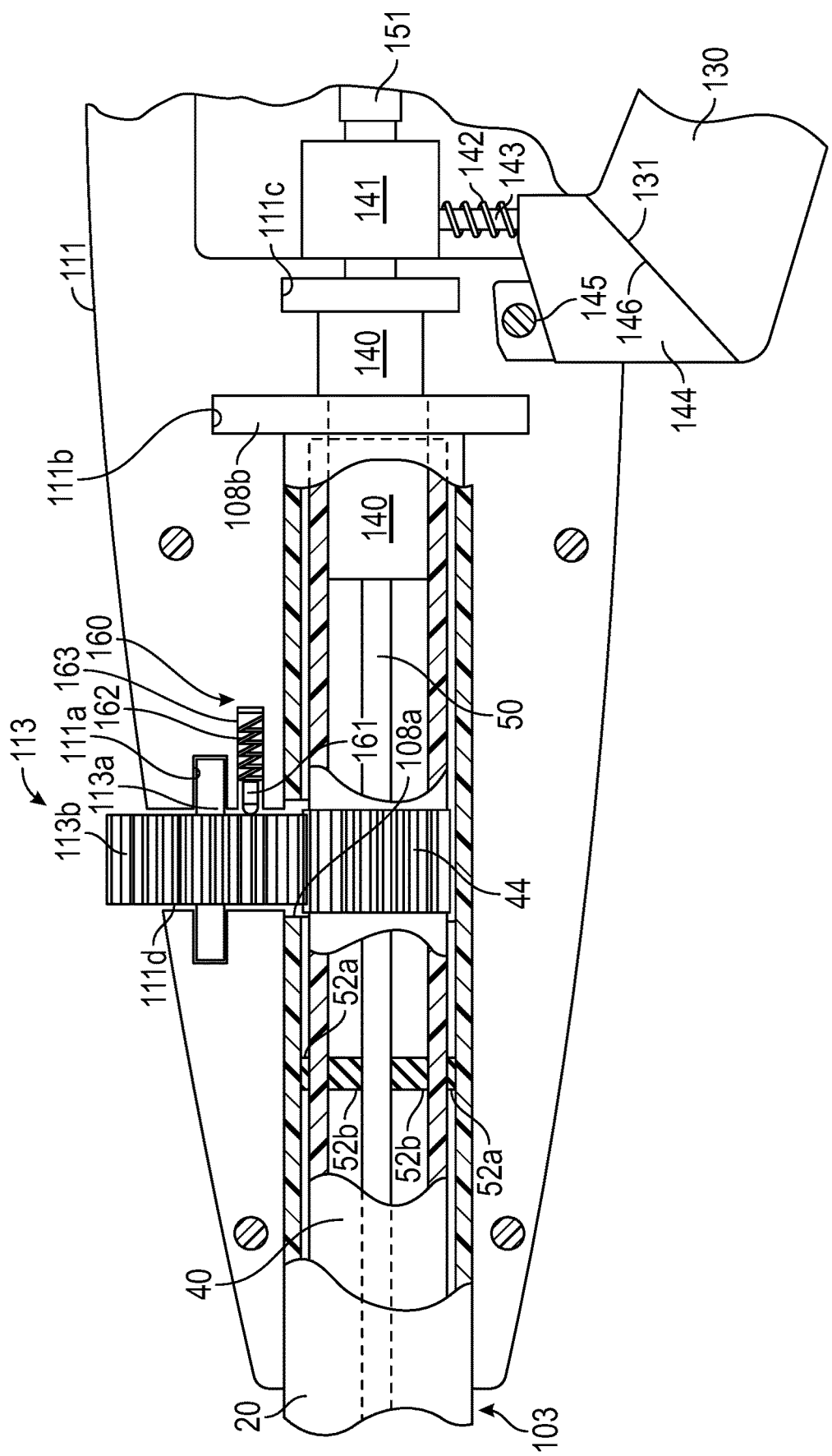
FIG. 6 is a partly sectional side view of a body portion of a surgical apparatus as described in at least one embodiment herein.
Figure 7:
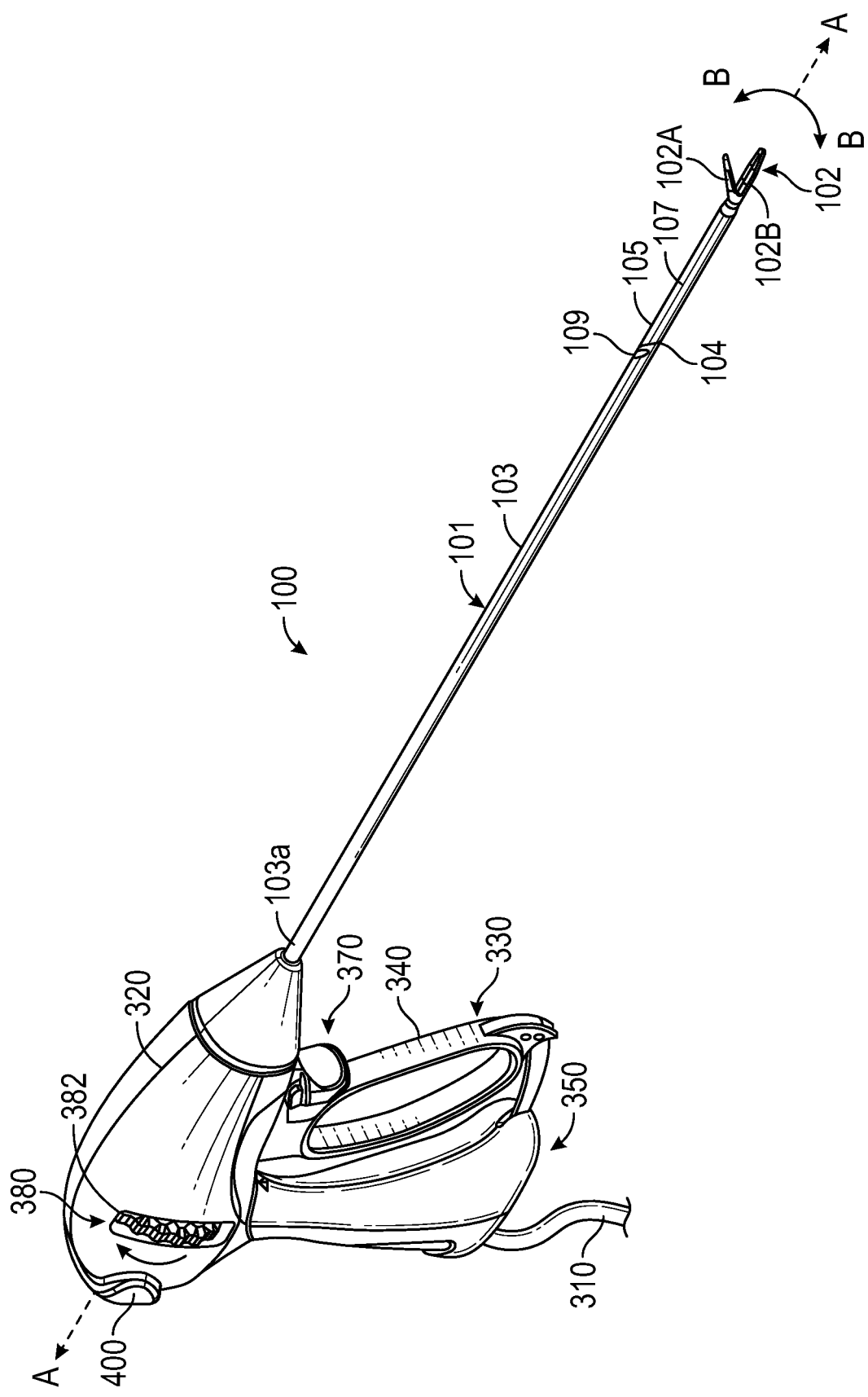
FIG. 7 is a perspective view of a surgical apparatus as described in at least one embodiment herein.

Referring now to FIG. 6, an alternative embodiment 200 of the apparatus is shown wherein the trigger 230 is connected to the rear portion of the handle grip 220.

Handle grip 220 and body portion 210 are pivotally connected at rotary interface 221 by means of a coupling 252, such as coupling 152 described above.

Endoscopic portion 201 is similar in operation to endoscopic portion 101 and is similarly actuated by means of rotary actuator 213.

An alternative hydraulically operated actuation mechanism 240 is employed, which comprises first and second cylindrical hydraulic chambers 241 and 242 containing a hydraulic fluid such as water, oil or other suitable liquid, and connected by means of two fluid carrying tubes 243 and 244.

A movable piston (not shown) is located in the interior of each hydraulic chamber. The piston in the first hydraulic chamber 241 is mechanically linked to trigger 230 by means of rod 245. The piston in the second hydraulic chamber 242 is mechanically linked to drive rod 205 for actuating the distal operating portion of the apparatus. When the apparatus 200 is actuated by pressing trigger 230, the trigger 230 pivots (clockwise, as shown) around pivot pin 231 and moves rod 245 out of first chamber 241, thereby forcing hydraulic fluid through tube 243 and into the distal end of the second chamber 242. The piston in the second chamber 242 is forced to move proximally, thereby pulling the drive rod 205 proximally and actuating the distal operating portion. Fluid exits the second hydraulic chamber 242 via line 244 and enters the first hydraulic chamber 241. Alternative configurations of the hydraulic tubes may be employed to move the drive rod distally instead of proximally. Also, hydraulic chamber 242 may alternatively incorporate a hydraulically driven rotor to turn drive rod 205 rather than move it linearly. Optionally, a spring 246 may be employed to bias the trigger 230 back to its initial position.

Turning now to FIG. 7, in some embodiments, the surgical apparatus is an endoscopic vessel sealing forceps 300 generally including a non-endoscopic portion 110 including a housing 320, a handle assembly 330, a rotating assembly 380, a trigger assembly 370, and a toggle switch 400, and an endoscopic portion 101 including a first segment 103, a second segment 105, an angled rotary interface joint 104, a channel 109, and a distal operating portion 107 which includes a tissue sealing unit including an end effector assembly 102. The end effector assembly 102 including a pair of opposing jaw members 102a, 102b which mutually cooperate to rotate, articulate, grasp, seal and divide tubular vessels and vascular tissue. The sealing forceps 300 for use in connection with endoscopic surgical procedures can be used for bipolar surgical procedures or monopolar surgical procedures which employ a remote patient pad for completing the current loop.

Housing 320 is operatively connected to a first proximal end portion 103b of the first segment 103. Housing 320 is connected to handle assembly 330 which includes a fixed handle 350 and a movable handle 340. Fixed handle 350 is integrally associated with housing 320 and handle 340 is movable relative to fixed handle 350. Movable handle 340 can be connected to a drive assembly (not shown) which, together, mechanically cooperate to impart movement of the jaw members 102a, 102b from an open position wherein the jaw members 102a, 102b are disposed in spaced relation relative to one another, to a clamping or closed position wherein the jaw members 102a, 102b cooperate to grasp tissue therebetween.

Rotating assembly 380 may also be integrally associated with the housing 320 and is configured to rotate the end effector 102 via rotating wheel 382 approximately 180 degrees in either direction about a longitudinal axis "A-A" defined through endoscopic portion 101.

As further depicted in FIG. 7, forceps 300 also includes an electrosurgical cable 310 which connects the forceps 300 to a power source suitable for electrosurgical energy. In some embodiments, the power source can be a generator (not shown). In some embodiments, the power source can be a battery (not shown).

Cable 310 can be divided internally into one or more cable wires or leads which each transmit electrosurgical energy through their respective feed paths through the forceps 300. One set of cable wires or leads can extend from cable 310 and connect electrically the joy-stick-like toggle switch 400 with the end effector 102 for sealing tissue. It is envisioned that actuation of the switch 400 permits the user to selectively activate the jaw members 102a, 102b to seal tissue.

It is further envisioned that another set of cable wires or leads can extend from cable 310 and connect trigger assembly 70 to a motor (not shown) located inside housing 320. The motor connected to a proximal end portion of a rotary driver. Actuation of the trigger assembly 370 would permit the user to selectively activate rotation of the rotary driver via the motor (as opposed to the manual actuator 113) causing the second segment 105 to articulate or rotate around the angled rotary interface joint 104 via the first and second beveled gears and the angled gear as described herein. As can be appreciated, automation of the rotary driver can accelerate and/or simplify the articulation process.

Figure 8:
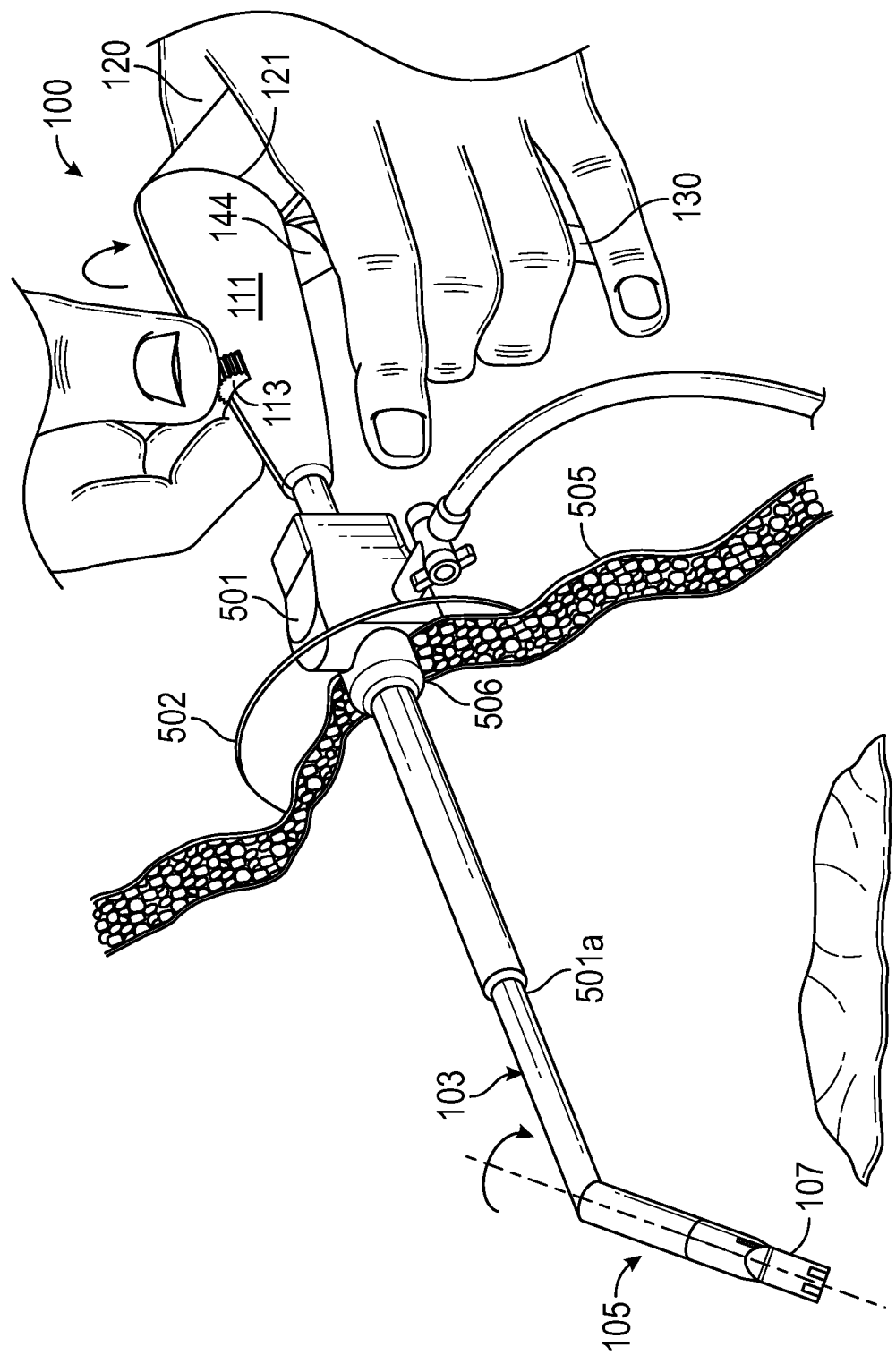
FIG. 8 is a perspective view illustrating a method of use of a surgical apparatus as described herein in an endoscopic surgical procedure.

Referring now to FIG. 8, a method of using the present surgical apparatus is illustrated. A cannula assembly 501 such as commonly used in endoscopic procedures is stabilized by a patch 502 and inserted through an incision 506 in a wall of body tissue 505. Apparatus 100 is inserted through the cannula assembly 501 until the second segment 105 is fully within the body cavity and beyond the distal end 501a of the cannula.

To position the distal operating portion 107 the surgeon turns actuator 113 to angle the second segment 105. The distal operating portion 107 may then be actuated by pressing trigger 130.

Prior to removal, the surgeon can turn actuator 113 again until the second segment 105, including distal operating portion 107, is returned to a collinear configuration with first segment 103 and cannula assembly 501a.

In some embodiments, the apparatus described herein may be used in a method for surgically operating on body tissue in the interior of a body cavity. Such a method may include: inserting an endoscopic portion of a surgical apparatus described herein through a cannula assembly into the body cavity; positioning a distal operating portion of the apparatus at an operating site; and actuating said distal operating portion. In such embodiments, the surgical apparatus includes a non-endoscopic portion and an endoscopic portion. The endoscopic portion ht least a first segment, a second segment, and the distal operation portion. The first segment including a first proximal end portion operatively connected to the non-endoscopic portion and a first distal end portion connected to a second proximal end portion of the second segment by at least one angled rotary interface joint, the first distal end portion including a first beveled gear and a second beveled gear, the second beveled gear positioned between the first beveled gear and an angled gear affixed on the second proximal end portion of the second segment, and the distal operating portion connected to a second distal end portion of the second segment.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A surgical apparatus for use in minimally invasive surgical procedures, which comprises:

a) non-endoscopic portion; and
   b) an endoscopic portion having at least first and second segments connected by at least one angled rotary interface joint, the first segment including a first proximal end portion operatively connected to the non-endoscopic portion and a first distal end portion including a first beveled gear and a second beveled gear, the second beveled gear positioned between the first beveled gear and an angled gear affixed on a second proximal end portion of the second segment.

2. The surgical apparatus according to claim 1, wherein the first segment includes a first outer wall defining a first lumen along a first longitudinal axis defined between the first proximal end portion and the first distal end portion, wherein the first and second beveled gears are positioned within the lumen.

3. The surgical apparatus according to claim 2, wherein the first outer wall further comprises an angled circumferential channel defined therethrough configured to receive at least a portion of the angled gear.

4. The surgical apparatus according to claim 3, wherein the angled circumferential channel is configured to receive a third set of alternating teeth and slots extending radially outward from a side of the angled gear.

5. The surgical apparatus according to claim 4, wherein at least a portion of the third set of alternating teeth and slots of the angled gear extend through the angled circumferential channel and beyond an outer surface of the outer wall.

6. The surgical apparatus according to claim 1, wherein the first beveled gear faces distally along the first longitudinal axis and further comprises a rotary driver extending proximally along the first longitudinal axis to the non-endoscopic portion.

7. The surgical apparatus according to claim 1, wherein the second beveled gear is positioned on a post positioned distal to the first beveled gear, the post extending generally perpendicular to the first longitudinal axis and affixed on an inner surface of the first outer wall.

8. The surgical apparatus according to claim 1, wherein the second segment includes a second outer wall defining a second lumen along a second longitudinal axis defined between the second proximal end portion and a second distal end portion, wherein the second longitudinal axis and the first longitudinal axis are collinear when the endoscopic portion is straight.

9. The surgical apparatus according to claim 8, wherein the second segment is configured to rotate about the angled rotary interface joint so the second longitudinal axis of the segment is about 90° relative to the first longitudinal axis of the first segment.

10. The surgical apparatus according to claim 1, wherein the first distal end portion of the first segment further includes a first angled edge spaced distally from the angled circumferential channel by a first length and the second proximal end portion of the second segment further includes a second angled edge spaced distally from the angled gear by a gap defined by a sidewall having a second length.

11. The surgical apparatus according to claim 10, where the first length and the second length are about the same.

12. The surgical apparatus according to claim 1, wherein the first beveled gear includes a first set of alternating teeth and slots configured to mechanically interact with a second set of alternating teeth and slots of the second beveled gear, and the second set of alternating teeth and slots are also configured to mechanically interact with a third set of alternating teeth and slots of the angled gear.

13. The surgical apparatus according to claim 1, further comprising a distal operating portion operatively coupled to a second distal end portion of the second segment.

14. The surgical apparatus according to claim 13, wherein the distal operating portion comprises a surgical unit selected from the group consisting of a surgical stapler unit, surgical retractor unit, surgical sealer unit, surgical ablation unit, or clip applier unit.

15. The surgical apparatus according to claim 14, wherein the non-endoscopic portion comprises a body portion including a housing having an interior longitudinal bore, the rotary drive tube disposed within the interior longitudinal bore of the housing, the body portion including a rotary actuator disk rotatably mounted to the housing and operatively engaged with the rotary drive tube such that rotation of the rotary actuator disk effects rotation of the rotary drive tube.

16. The surgical apparatus according to claim 15, wherein the proximal end portion of the rotary drive tube possesses a circumferential array of teeth forming a first spur gear and the outer tube possesses a slot aligned with the array of teeth in the rotary drive tube, the rotary actuator disk possessing circumferential teeth forming a second spur gear, at least a portion of the rotary actuator disk being disposed through the slot in the outer tube so as to engage the first and second spur gears.

17. The surgical apparatus according to claim 16, wherein the surgical apparatus further comprises a drive cylinder and a push rod, the push rod extending through the endoscopic portion and operatively connected between the distal operating portion and the drive cylinder positioned with the body portion, wherein the push rod is linearly moved by the drive cylinder for actuating the distal operating portion.

18. The surgical apparatus according to claim 17, further comprising a trigger for actuating the drive cylinder, wherein the drive cylinder is pneumatically or hydraulically driven.

19. The surgical apparatus according to claim 1, wherein the surgical apparatus is a surgical retractor.

20. A surgical apparatus for use in minimally invasive surgical procedures, which comprises:
    a) non-endoscopic portion; and
    b) an endoscopic portion having at least first and second segments connected by at least one angled rotary interface joint including a first beveled gear, a second beveled gear, and an angled non-beveled gear, wherein the first beveled gear drives the angled non-beveled gear via the second beveled gear.

* * * * *